United States Patent [19]

O'Lenick, Jr. et al.

[11] Patent Number: 5,312,968
[45] Date of Patent: May 17, 1994

[54] FLUORINE CONTAINING GUERBET CITRATE ESTERS

[75] Inventors: Anthony J. O'Lenick, Jr., Lilburn, Ga.; Charles Buffa, Englewood, N.J.

[73] Assignees: Siltech Inc., Norcross, Ga.; Biosil Technologies Inc., Englewood, N.J.

[21] Appl. No.: 116,566

[22] Filed: Sep. 7, 1993

[51] Int. Cl.$^5$ .................. C07C 69/704; A61K 7/075; A61K 7/48; A61K 31/225
[52] U.S. Cl. ...................................... 560/182; 424/70
[58] Field of Search ... 560/182; 424/70, DIG. 1–DIG. 4; 518/547

[56] References Cited

U.S. PATENT DOCUMENTS

| | | | |
|---|---|---|---|
| 4,425,458 | 1/1984 | Lindner et al. | 524/314 |
| 4,731,190 | 3/1988 | O'Lenick | 252/49.3 |
| 4,767,815 | 8/1988 | O'Lenick | 524/317 |
| 4,868,236 | 9/1989 | O'Lenick | 524/308 |
| 5,260,401 | 11/1993 | O'Lenick, Jr. | 528/26 |

Primary Examiner—José G. Dees
Assistant Examiner—Barbara S. Frazier

[57] ABSTRACT

The present invention deals with the preparation, compositions, and application of certain high molecular weight hydrophobic fluorine containing guerbet citrate esters. These materials are useful in personal care products, most importantly skin care products and in plastic lubrication.

20 Claims, No Drawings

FLUORINE CONTAINING GUERBET CITRATE ESTERS

BACKGROUND OF THE INVENTION

1. Field of the Invention

The present invention deals with the preparation, compositions, and application of certain high molecular weight hydrophobic fluorine containing guerbet citrate esters. These materials are useful in personal care products, most importantly skin care products and as polycarbonate lubricants.

2. Description of the Art Practices

Guerbet alcohol and their simple esters are well known to those skilled in the art. Specific references to guerbet esters include:

U.S. Pat. No. 4,425,458 to Lindner and O'Lenick issued Jan. 10, 1984, teaches that specific guerbet alcohol diesters containing from 16 to 40 carbon atoms total in the guerbet alcohol molecule can be used as mold release agents in polycarbonate products.

U.S. Pat. No. 4,767,815 issued Aug. 30, 1988 to O'Lenick teaches that two mole equivalents of a guerbet alcohol can be reacted with butryolactone to form a ether ester which can be used as a polycarbonate lubricant.

U.S. Pat. No. 4,868,483 issued September 1989 to O'Lenick teaches the preparation of guerbet citrate tri esters. These esters lack the critical fluorine component which as will become clear make the compounds of the present invention function in a unique way on the skin and hair.

To the extent that each of the foregoing patents is relevant to the present invention they are herein specifically incorporated by reference. Throughout the specification and claims, percentages and ratios are by weight, pressures are gauge and temperatures are Celsius unless otherwise noted.

SUMMARY OF THE INVENTION

Object of the Invention

The present invention is directed to a series of high molecular weight highly branched citrate esters which contain an effective conditioning amount of fluorine which renders the ester spreadable and hydrophobic on the skin. The effective conditioning amount ranges from 0.5% Fluorine to 50% Fluorine. The fluorine part of the molecule renders spreadability, chemical resistance, water barrier properties and a dry feel when applied to the skin. Without the fluorine the compounds are oily, do not have an acceptable degree of spreadability and do not form breathable barriers.

The present invention is also directed to a series of high molecular weight highly branched fluorine containing citrate esters, useful as a mold release agent for polycarbonate resin compositions. It will be observed in the present invention that the mold release agents of this invention result in polycarbonate products in which the clarity is not adversely affected and quantities of mold release needed to obtain good release are much lower than those heretofore known. This is due to the presence of the fluorine in the molecule which results in very thin very uniform layer of lubricant which is present between the plastic and the metal surface of the mold. This improved spreadability is an unexpected benefit of incorporating the fluorine into the molecule. The esters of the present invention are observed to migrate sufficiently from the polycarbonate resin to the surface of the mold to effect release. These esters do not substantially sweat out or collect on the surface of the molded articles.

The Invention

The esters are the reaction product of a guerbet alcohol or a guerbet alcohol alkoxylate, citric acid and a flouro alcohol. The selection of a guerbet alcohol as a reactant for the preparation of the compounds of the present invention is also important in that this component renders superfatting and emmolient properties to the product.

Guerbet Alcohols have been known since the 1890's when Marcel Geurbet first synthesized these materials (M. Guerbet, C.R. Acad. Sci. Paris, 128, 511; 1002 (1989)). These materials are high in molecular weight and are liquid even at very low temperatures.

The guerbet alcohols used in the present invention contain from about 12 to 40 carbon atoms (total) in the guerbet alcohol molecule. Preferably, the total number of carbon atoms in the guerbet alcohol molecule will be from about 20 to 36 carbon atoms and in particular 20 carbon atoms in each guerbet alcohol.

It is known in the art that guerbet alcohols may be formed from the same or different alcohols i.e. a homo or hetero system. That is, a guerbet alcohol is the condensation product of two alcohol molecules joined at the beta carbon of the alcohol which has retained the hydroxyl functionality. The resultant product is therefore a highly branched primary alcohol containing a single hydroxyl group. It is possible to obtain mixtures of alcohols and to condense them into hetero systems.

Another aspect of the present invention is the application of the esters of the current invention to the skin for providing a thin non-occlusive hydrophobic coating to the skin. The incorporation of fluorine into the molecule results in spreadability of the ester on the skin, resulting in a thin coating. Compounds lacking the fluorine are oily and do not provide the dry feeling thin film.

DETAILED DESCRIPTION OF THE INVENTION

The present invention describes molecules that are guerbet citrate flouro esters. The presence of the fluorine in the molecule is particularly important in that it gives very desirable properties to the resultant ester for use on skin. Incorporation of polyoxypropylene and or polyoxyethylene into the ester results in the increased ability to alter the solubility of the ester in many organic solvents.

The molecules of this invention conform to the following generic structure:

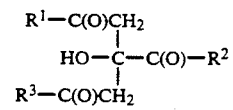

wherein; $R^1$ and $R^2$ are independently

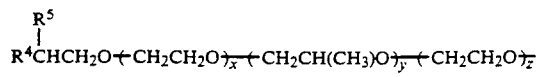

$R^3$ is

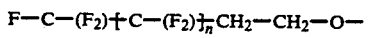

wherein:
n is ranges from 3 to 17;
$R^4$ and $R^5$ are each independently alkyl having from 4 to 20 carbon atoms;
x, y and z are independently between 0 and 20.

In a preferred range $R^4$ and $R^5$ each independently range from $C_6H_{13}$ to $C_{10}H_{21}$ and x, y and z each independently range from 0 to 5.

The invention relates to a series of guerbet flouroester which is prepared by the esterification reaction of;
(a) citric acid;
(b) a guerbet alcohol conforming to the following structure;

wherein;
$R^4$ and $R^5$ are each independently alkyl having from 4 to 20 carbon atoms;
x, y and z are independently between 0 and 20;
The term "alkyl" as used herein refers to a compound having the following generic structure $C_n H_{2n+1}$
(c) a flouro alcohol conforming to the following structure;

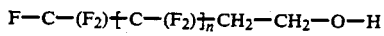

wherein: n is ranges from 3 to 17;

The esterification reaction can be conducted without catalyst; however, when no catalysts used reaction rates are inefficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. Preferred is stannous oxylate. The reaction is conducted at between 140 and 240 C.

EXAMPLES

Raw Materials

Guerbet Alcohols and Alkoxylates

The Guerbet alcohols used as raw materials are items of commerce and are prepared by processes known to those skilled in the art. They are produced by several manufacturers most importantly Nova Molecular Technologies, Lake Geneva Wi.

The alcohols were ethoxylated using standard procedures known to those skilled in the art. Reference is drawn to U.S. Pat. No. 4,731,190 to O'Lenick, Jr. et al, which is incorporated herein by reference. The patent teaches the alkoxylation processes for guerbet alcohols.

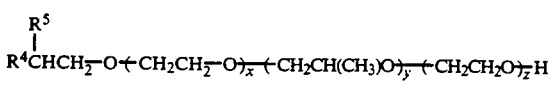

| Example | $R^4$ | $R^5$ | x | y | z |
|---|---|---|---|---|---|
| 1 | C8 | C10 | 0 | 0 | 0 |
| 2 | C8 | C10 | 1 | 1 | 1 |
| 3 | C8 | C10 | 0 | 5 | 2 |
| 4 | C8 | C10 | 5 | 5 | 5 |
| 5 | C8 | C10 | 10 | 10 | 10 |
| 6 | C11 | C13 | 0 | 0 | 0 |
| 7 | C11 | C13 | 1 | 1 | 1 |
| 8 | C11 | C13 | 0 | 5 | 2 |
| 9 | C11 | C13 | 5 | 5 | 5 |
| 10 | C11 | C13 | 10 | 10 | 10 |
| 11 | C16 | C18 | 0 | 0 | 0 |
| 12 | C16 | C18 | 1 | 1 | 1 |
| 13 | C16 | C18 | 0 | 5 | 2 |
| 14 | C16 | C18 | 5 | 5 | 5 |
| 15 | C16 | C18 | 10 | 10 | 10 |

Citric Acid

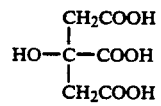

Fluorine Containing Alcohols

Fluorine containing alcohols are commercially available from a variety of suppliers, most importantly DuPonte Performance Products Division. They conform to the following structure;

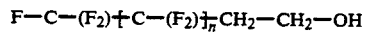

n is ranges from 3 to 17.

| Reactant Example Number | n Value | Molecular Weight | % F |
|---|---|---|---|
| 16 | 3 | 264 | 64.7 |
| 17 | 5 | 364 | 67.8 |
| 18 | 7 | 464 | 69.6 |
| 19 | 9 | 564 | 70.7 |
| 20 | 11 | 664 | 71.5 |
| 21 | 13 | 764 | 72.1 |
| 22 | 15 | 864 | 72.5 |
| 23 | 17 | 964 | 72.9 |

Reaction Conditions

The esterification can be run without catalyst; however, when no catalysts used reaction rates are inefficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. Preferred is stannous oxylate. The reaction is conducted at between 140 and 240 C. under an inert nitrogen blanket. Preferred temperature range is between 180 and 210 C. Water is removed from the reaction which is done using a nitrogen sparge or vacuum of up to 10 mm.

The following are suggested embodiments of present invention.

EXAMPLE 24

To a suitable reaction vessel is added 296.0 guerbet alcohol example 1, 64.0 grams of citric acid and 121.0 grams of fluoro alcohol Example 17 and 2.0 grams of stannous oxylate catalyst. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without additional purification.

|  | Guerbet Alkoxylate | | Fluoro Alcohol | |
| --- | --- | --- | --- | --- |
| Example | Example | Grams | Example | Grams |
| 25 | 1 | 200.0 | 16 | 88.0 |
| 26 | 2 | 296.0 | 17 | 121.0 |
| 27 | 3 | 453.0 | 18 | 155.0 |
| 28 | 4 | 688.6 | 19 | 189.0 |
| 29 | 5 | 1,178.5 | 20 | 221.0 |
| 30 | 6 | 254.0 | 21 | 254.0 |
| 31 | 7 | 351.4 | 22 | 288.0 |
| 32 | 8 | 508.8 | 22 | 28.0 |
| 33 | 9 | 743.0 | 16 | 88.0 |
| 34 | 10 | 1,232.3 | 17 | 121.0 |
| 35 | 11 | 347.5 | 18 | 155.0 |
| 36 | 12 | 446.0 | 19 | 189.0 |
| 37 | 13 | 602.7 | 20 | 221.0 |
| 38 | 14 | 837.1 | 21 | 254.0 |
| 39 | 15 | 1,326.7 | 22 | 288.0 |
| 40 | 1 | 200.0 | 17 | 12.1 |
| 41 | 1 | 200.0 | 16 | 88.0 |
| 42 | 1 | 200.0 | 17 | 121.0 |
| 43 | 1 | 200.0 | 18 | 155.0 |
| 44 | 1 | 200.0 | 19 | 189.0 |
| 45 | 1 | 200.0 | 20 | 221.0 |
| 46 | 6 | 254.0 | 21 | 254.0 |
| 47 | 6 | 254.0 | 22 | 288.0 |
| 48 | 6 | 381.0 | 16 | 8.8 |
| 49 | 6 | 254.0 | 16 | 88.0 |
| 50 | 6 | 254.0 | 17 | 121.0 |
| 51 | 12 | 446.0 | 18 | 155.0 |
| 52 | 12 | 446.0 | 19 | 189.0 |
| 53 | 12 | 446.0 | 20 | 221.0 |
| 54 | 12 | 446.0 | 21 | 254.0 |
| 55 | 12 | 446.0 | 22 | 288.0 |
| 56 | 12 | 446.0 | 19 | 18.9 |

APPLICATIONS EXAMPLES

1. Hydrophobic Materials

The compounds of Example 35 and 50 were evaluated against Siltech CE-2000 (a non-fluorinated tri guerbet citrate) on the skin by an independent laboratory (Barlo Laboratories Merrick, N.Y.). The analysis indicated that there are several significant unexpected differences between the fluorine containing and the non-fluoro containing products, which include;
1. The fluorine products have much superior cushion.
2. The fluorine products contribute much greater emoliency to the skin than do the non flouro containing materials.
3. The fluorine products make the skin retain more moisture forming a breathable non-occlusive barrier.
4. The fluoro products form thinner films on the skin, allowing for a more comfortable feel.

All of these properties make the compounds of the present invention superior to the non-fluorinated products.

2. Ethoxylated Materials

The inclusion of ethylene oxide into the fluoro containing molecules results in water dispersible product which can be applied to the hair to form barriers which resist dirt, and environmental contaminants, improve wet combability and provides outstanding gloss to the hair. For this evaluation, example 34 was diluted in water to a concentration of 5%.

3. Polycarbonate Lubrication

The polycarbonate compounds with which the present esters are effective mold release agents include homopolycarbonates and copolycarbonates which are based, for example, on one or more of the following bisphenols: hydroquinone, resorcinol, dihydroxydiphenyls, bis-(hydroxyphenyl)-alkanes, bis-(hydroxyphenyl)-cycloalkanes, bis-(hydroxylphenyl)-sulphides, bis-(hydroxyphenyl)-ethers, bis-(hydroxylphenol)-ketones, bis-(hydroxyphenyl)-sulphoxides, bis-(hydroxyphenyl)-sulphones and alpha, alpha-bis(hydroxyphenyl)-diisopropyl-benzenes, as well as their nuclear alkylated and nuclear-halogenated compounds.

The aromatic polycarbonates can be prepared in accordance with known processes, such as, for example, in accordance with the melt trans-esterification process from bisphenols and diphenyl carbonate and the two-phase boundary process from bisphenols and phosgene, as described in the above mentioned literature.

The aromatic high-molecular weight polycarbonates can be branched due to the incorporation of small amounts, preferably of between 0.05 and 2.0 mol % (relative to diphenols employed), of trifunctional or more than trifunctional compounds, especially compounds with three of more phenolic hydroxyl groups. Polycarbonates of this type are described, for example, in German Offenlegungsschriften (German Published Specifications) Nos. 1,570,533, 1,595,762, 2,116,974 and 2,113,347; British Patent Specification No. 1,079,821; U.S. Pat. No. 3,544,514 (which is incorporated herein by reference).

What is claimed is:

1. A guerbet flouro-ester which is prepared by the esterification reaction of;
   (a) citric acid
   (b) a guerbet alcohol conforming to the following structure;

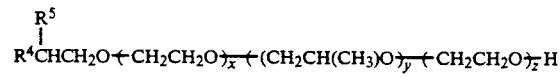

$R^4$ and $R^5$ are each independently alkyl having from 4 to 20 carbon atoms;
   x, y and z are independently between 0 and 20; and

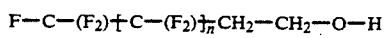

wherein: n is ranges from 3 to 17.
2. A compound of claim 1 wherein n is 3.
3. A compound of claim 1 wherein n is 5.
4. A compound of claim 1 wherein n is 7.
5. A compound of claim 1 wherein n is 9.
6. A compound of claim 1 wherein n is 11.
7. A compound of claim 1 wherein n is 13.
8. A compound of claim 1 wherein x, y and z are all zero.
9. A guerbet flouro-ester which conforms to the following structure:

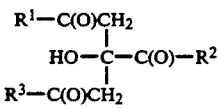

wherein;
R$^1$ and R$^2$ are independently

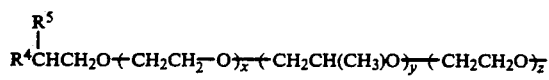

R$^4$ and R$^5$ are each independently alkyl having from 4 to 20 carbon atoms;
x, y and z are independently between 0 and 20;
R$^3$ is

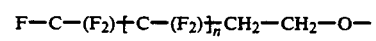

wherein: n is ranges from 3 to 17.

10. A process for treating skin which comprises contacting the skin with an effective conditioning amount of a guerbet fluoro citrate which is prepared by the esterification reaction of;
(a) citric acid
(b) a guerbet alcohol conforming to the following structure;

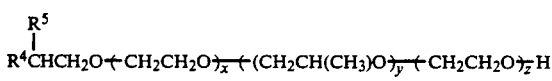

R$^4$ and R$^5$ are each independently alkyl having from 4 to 20 carbon atoms;
x, y and z are independently between 0 and 20; and

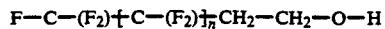

wherein: n is ranges from 3 to 17.

11. A process of claim 10 wherein said effective conditioning amount ranges from 0.1 to 5.0% by weight.

12. A process for treating hair which comprises contacting the hair with an effective conditioning amount of a guerbet fluoro citrate which conforms to the following structure:

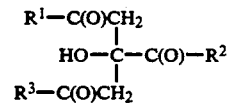

wherein;
R$^1$ and R$^2$ are independently

R$^4$ and R$^5$ are each independently alkyl having from 4 to 20 carbon atoms;
x, y and z are independently between 0 and 20;
R$^3$ is

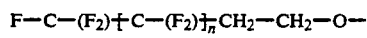

wherein: n is ranges from 3 to 17.

13. A process of claim 12 wherein said effective conditioning amount ranges from 0.1 to 5.0% by weight.
14. A process of claim 12 wherein n is 3.
15. A process of claim 12 wherein n is 5.
16. A process of claim 12 wherein n is 7.
17. A process of claim 12 wherein n is 9.
18. A process of claim 12 wherein n is 11.
19. A process of claim 12 wherein n is 13.
20. A process of claim 1 wherein x, y and z are all zero.

* * * * *